(12) United States Patent
Ishikawa et al.

(10) Patent No.: US 12,076,180 B2
(45) Date of Patent: Sep. 3, 2024

(54) IMAGE PROCESSING APPARATUS, ULTRASOUND DIAGNOSTIC APPARATUS, AND IMAGE PROCESSING METHOD

(71) Applicant: Canon Medical Systems Corporation, Otawara (JP)

(72) Inventors: Hiroaki Ishikawa, Saitama (JP); Satoshi Matsunaga, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 341 days.

(21) Appl. No.: 17/152,896

(22) Filed: Jan. 20, 2021

(65) Prior Publication Data

US 2021/0228178 A1  Jul. 29, 2021

(30) Foreign Application Priority Data

Jan. 23, 2020  (JP) ................. 2020-009215

(51) Int. Cl.
*A61B 8/08* (2006.01)
*A61B 8/00* (2006.01)
*G06T 7/00* (2017.01)

(52) U.S. Cl.
CPC ............ *A61B 8/0825* (2013.01); *A61B 8/463* (2013.01); *A61B 8/466* (2013.01); *A61B 8/469* (2013.01); *G06T 7/0012* (2013.01); *G06T 2207/10136* (2013.01); *G06T 2207/30068* (2013.01); *G06T 2207/30208* (2013.01)

(58) Field of Classification Search
CPC ....... A61B 8/0825; A61B 8/463; A61B 8/466; A61B 8/469; G06T 7/0012; G06T 2207/10136; G06T 2207/30068; G06T 2207/30208
See application file for complete search history.

(56) References Cited

U.S. PATENT DOCUMENTS

| 10,157,465 B2 | 12/2018 | Sugiyama et al. |
| 2009/0312640 A1* | 12/2009 | Wang ............... A61B 6/502 600/443 |
| 2011/0021888 A1 | 1/2011 | Sing et al. |
| 2012/0014578 A1 | 1/2012 | Karssemeijer et al. |
| 2013/0101083 A1 | 4/2013 | O'Connor |

(Continued)

FOREIGN PATENT DOCUMENTS

| JP | 2012-213484 A | 11/2012 |
| JP | 2012-531276 A | 12/2012 |

(Continued)

OTHER PUBLICATIONS

Office Action mailed Jun. 13, 2023 in Japanese Application No. 2020-009215 filed Jan. 23, 2020.

*Primary Examiner* — Vu Le
*Assistant Examiner* — Winta Gebreslassie
(74) *Attorney, Agent, or Firm* — Oblon, McClelland, Maier & Neustadt, L.L.P.

(57) ABSTRACT

According to one embodiment, an image processing apparatus includes processing circuitry. The processing circuitry calculates, based on a region of interest set in a mammographic image, a first distance from the region of interest to a body surface on the mammographic image, and displays, in an ultrasound image, a marker indicating a position of the region of interest as viewed in a depth direction based on the first distance.

16 Claims, 13 Drawing Sheets

(56) References Cited

U.S. PATENT DOCUMENTS

2014/0236001 A1* 8/2014 Kondou ............... A61B 8/0841
                                                        600/440
2017/0128037 A1   5/2017 Mori et al.
2019/0000318 A1* 1/2019 Caluser ............... A61B 5/0073

FOREIGN PATENT DOCUMENTS

| JP | 2013-530394 A | 7/2013 |
| JP | 2013-150825   | 8/2013 |
| JP | 2015-027450 A | 2/2015 |
| JP | 2017-23834    | 2/2017 |
| JP | 2017-086896 A | 5/2017 |

* cited by examiner

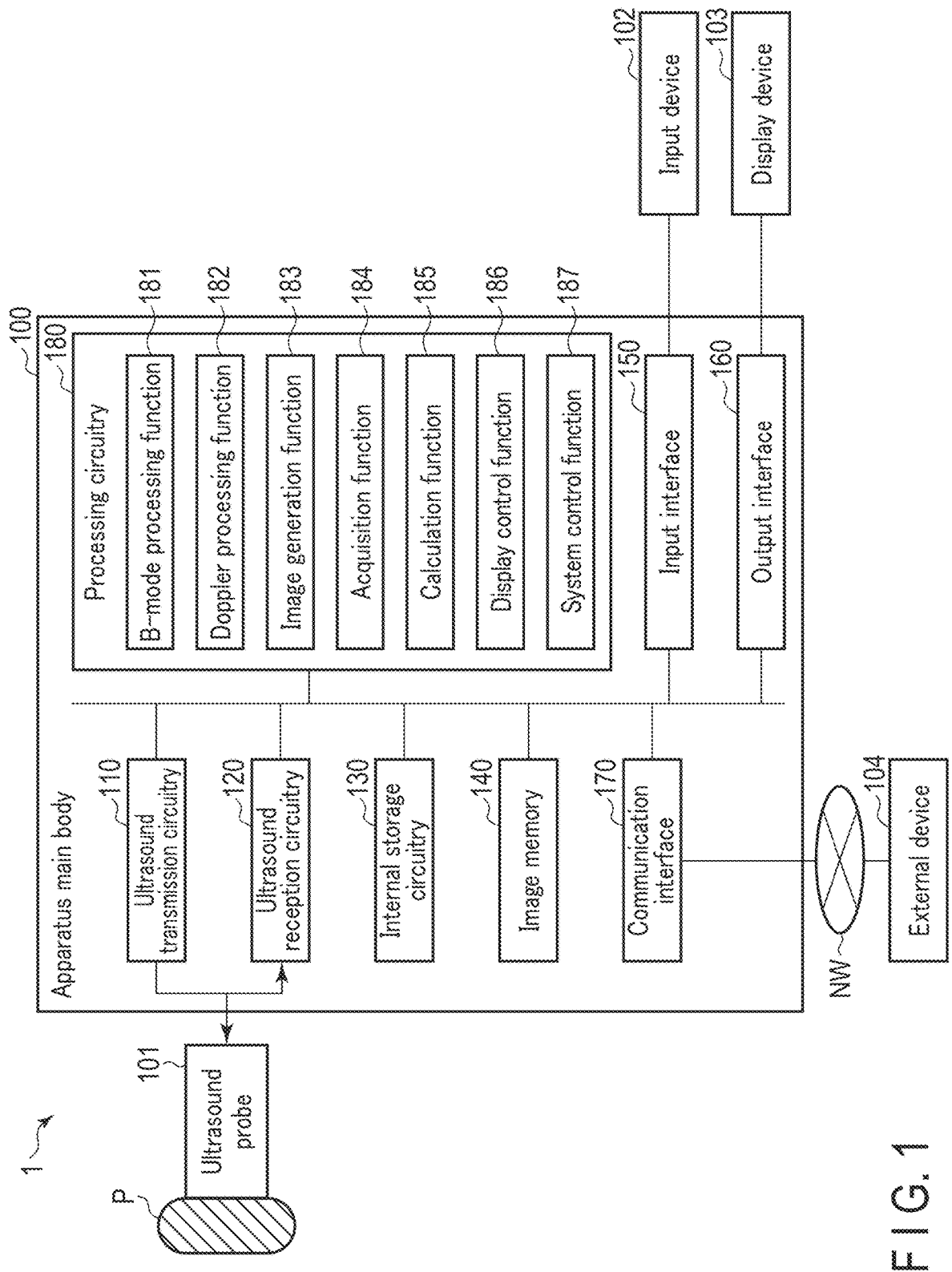
F I G. 1

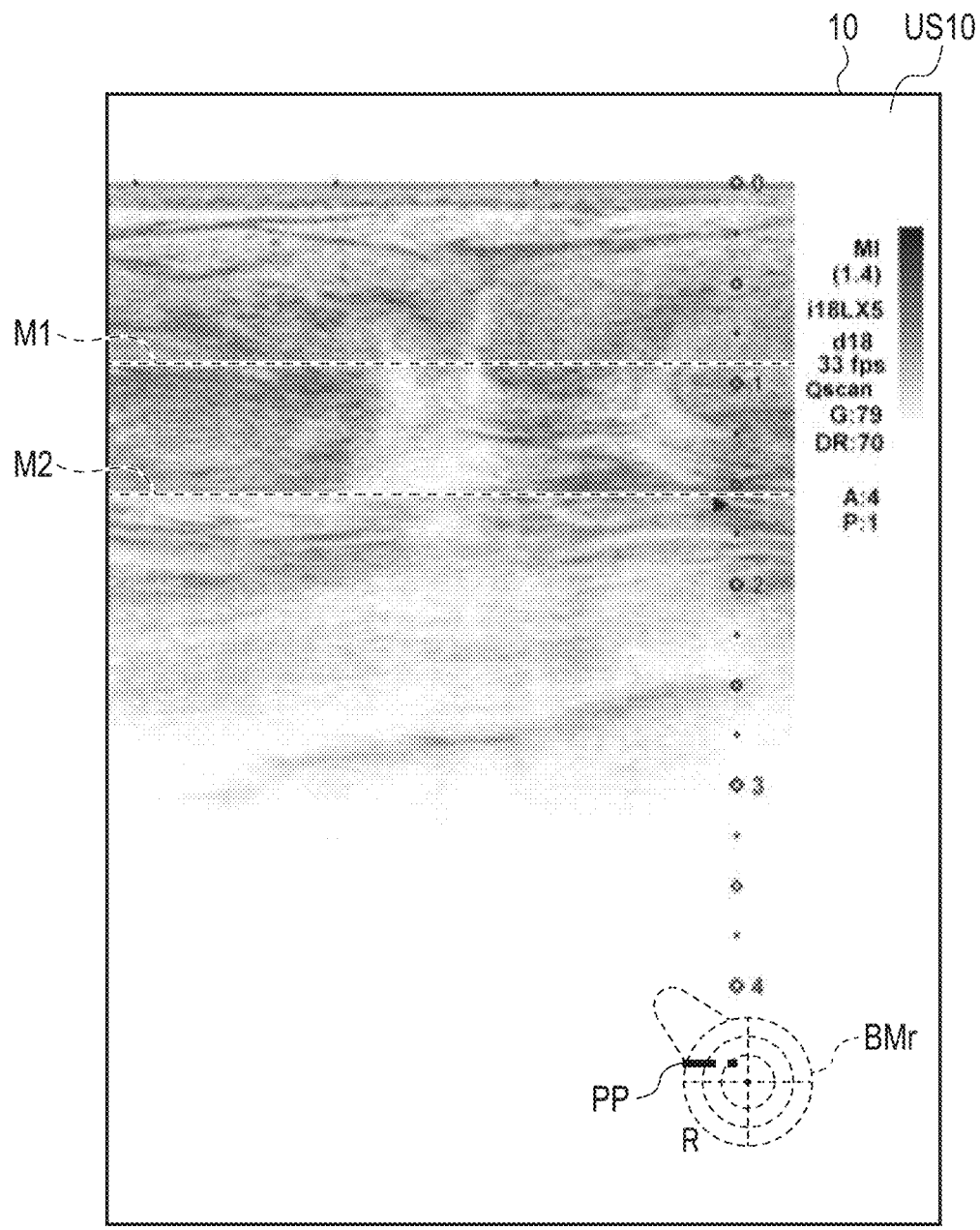
F I G. 5

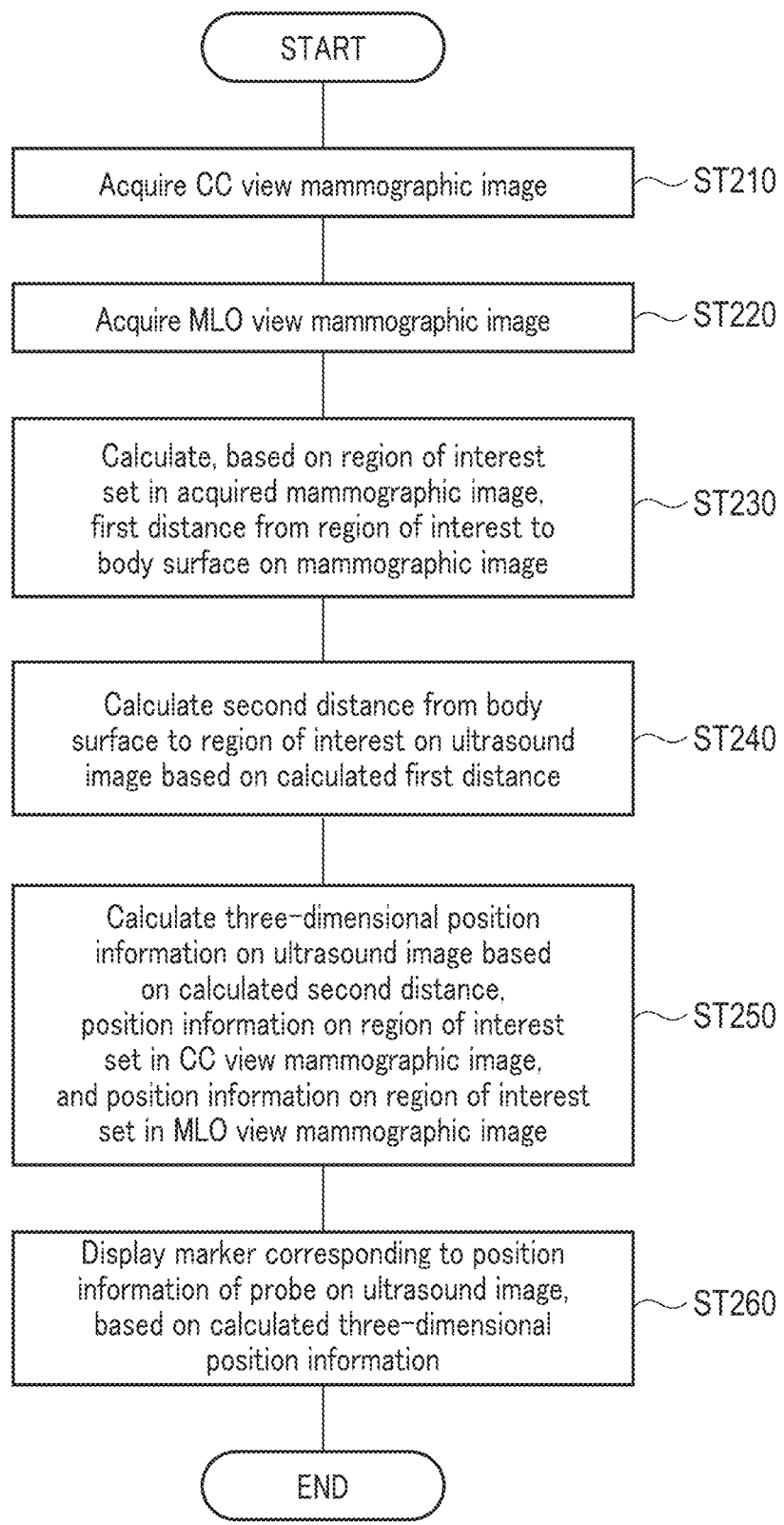
F I G. 7

IMAGE PROCESSING APPARATUS, ULTRASOUND DIAGNOSTIC APPARATUS, AND IMAGE PROCESSING METHOD

CROSS-REFERENCE TO RELATED APPLICATIONS

This application is based upon and claims the benefit of priority from Japanese Patent Application No. 2020-009215, filed Jan. 23, 2020, the entire contents of which are incorporated herein by reference.

FIELD

Embodiments described herein relate generally to an image processing apparatus, an ultrasound diagnostic apparatus, and an image processing method.

BACKGROUND

In mammographic image diagnosis used for breast cancer screening, etc., an examination based on an ultrasound image has recently been being performed after an examination based on a mammographic image. In accordance therewith, a function of setting (pointing at) a region of interest at a desired position on a mammographic image, and depicting a line, etc. corresponding to the position of the region of interest on a body mark of a breast has been developed. This function will be referred to as an "ultrasound diagnosis support function", since it supports a later examination based on an ultrasound image by depicting a line, etc. corresponding to the position of the region of interest.

However, the position of the region of interest as viewed in the depth direction is not expressed in such a body mark in which the region of interest is depicted. This demands that the operator read the depth-direction position from the region of interest on the mammographic image, and estimate the position on the ultrasound image.

BRIEF DESCRIPTION OF THE DRAWINGS

FIG. 1 is a block diagram showing a configuration example of an ultrasound diagnostic apparatus according to the first embodiment.

FIG. 5 is a first display example in which a marker display process has been performed according to the first embodiment.

FIG. 7 is a flowchart illustrating an example of an operation of a marker display process according to a second embodiment.

DETAILED DESCRIPTION

Figure 2:
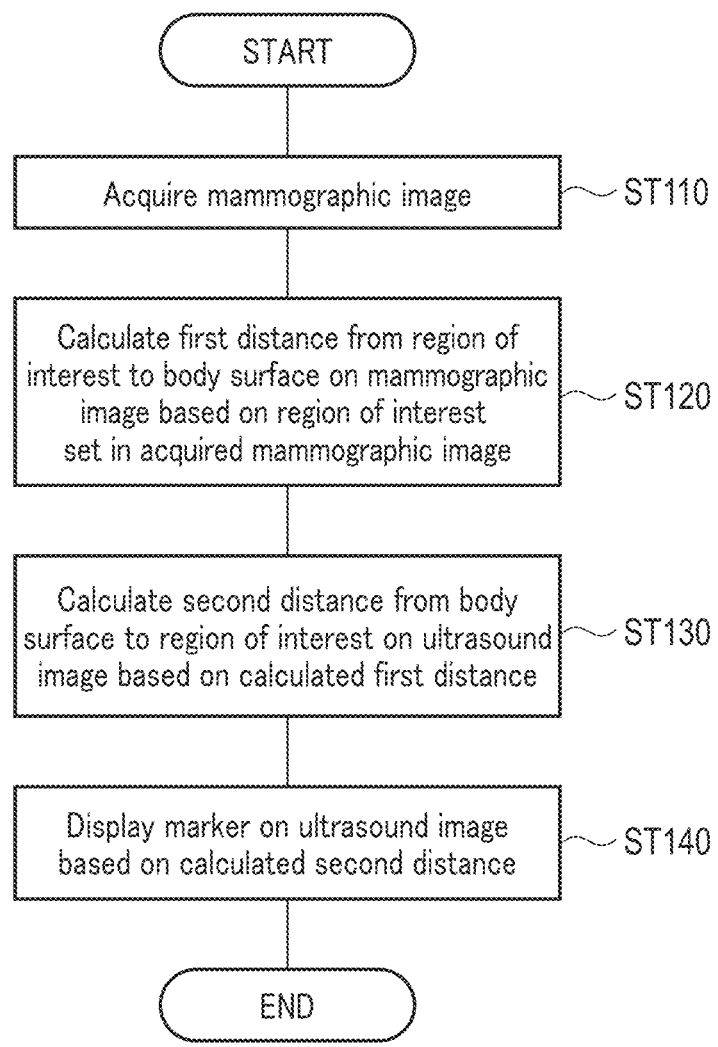
FIG. 2 is a flowchart illustrating an example of an operation of a marker display process according to the first embodiment.

In general, according to one embodiment, an image processing apparatus includes processing circuitry. The processing circuitry calculates, based on a region of interest set in a mammographic image, a first distance from the region of interest to a body surface on the mammographic image, and displays, in an ultrasound image, a marker indicating a position of the region of interest as viewed in a depth direction based on the first distance.

Hereinafter, embodiments of an ultrasound diagnostic apparatus and an image processing apparatus will be described in detail with reference to the accompanying drawings.

First Embodiment

FIG. 1 is a diagram showing a configuration example of an ultrasound diagnostic apparatus according to a first embodiment. An ultrasound diagnostic apparatus 1 shown in FIG. 1 includes an apparatus main body 100 and an ultrasound probe 101. The apparatus main body 100 is connected to an input device 102 and a display device 103. The apparatus main body 100 is connected to an external device 104 via a network NW. The external device 104 is, for example, a server on which a picture archiving and communication system (PACS) is installed.

The ultrasound probe 101 performs, for example, an ultrasound scan of a scan area in a living body P, which is the subject, under the control of the apparatus main body 100. The ultrasound probe 101 includes, for example, a plurality of piezoelectric transducers, a matching layer provided in each of the piezoelectric transducers, and a backing material that prevents propagation of the ultrasound wave from the piezoelectric transducers to the rear side. The ultrasound probe 101 is, for example, a one-dimensional array linear probe in which a plurality of ultrasound transducers are arranged in a predetermined direction. The ultrasound probe 101 is detachably connected to the apparatus main body 100. The ultrasound probe 101 may be provided with a button which is pressed in an offset process or in a freezing operation that freezes an ultrasound image.

The piezoelectric transducers generate an ultrasound wave based on a drive signal supplied from ultrasound transmission circuitry 110 (to be described later) included in the apparatus main body 100. Thereby, the ultrasound wave is transmitted from the ultrasound probe 101 to the living body P. When the ultrasound wave is transmitted from the ultrasound probe 101 to the living body P, the transmitted ultrasound wave is sequentially reflected by surfaces where the acoustic impedance becomes discontinuous in the living tissue of the living body P, and are received by a plurality of piezoelectric elements as reflected wave signals. The amplitude of the received reflected wave signal is dependent on differences in acoustic impedance at the surfaces where the ultrasound waves are reflected, causing the discontinuity in the acoustic impedance. When the transmitted ultrasound pulse is reflected by flowing blood or a surface such as a cardiac wall, the reflected wave signal is subjected to a frequency shift by the Doppler effect, depending on a velocity component in the ultrasound transmission direction of the moving object. Upon receiving the reflected wave signal from the living body P, the ultrasound probe 101 converts the reflected wave signal into an electric signal.

In FIG. 1, a connection relationship between a single ultrasound probe 101 and the apparatus main body 100 is shown as an example. However, a plurality of ultrasound probes may be connected to the apparatus main body 100. Which of the connected ultrasound probes is to be used for an ultrasound scan can be discretionarily selected by a switching operation.

The apparatus main body 100 is an apparatus that generates an ultrasound image based on a reflected wave signal received by the ultrasound probe 101. The apparatus main body 100 includes ultrasound transmission circuitry 110, ultrasound reception circuitry 120, internal storage circuitry 130, an image memory 140, an input interface 150, an output interface 160, a communication interface 170, and processing circuitry 180.

The ultrasound transmission circuitry 110 is a processor that supplies a drive signal to the ultrasound probe 101. The ultrasound transmission circuitry 110 is implemented by, for example, trigger generation circuitry, delay circuitry, pulse circuitry, etc. The trigger generation circuitry repeatedly generates a rate pulse for forming transmission ultrasound waves at a predetermined rate frequency. The delay circuitry provides each rate pulse generated by the trigger generation circuitry with a delay time for each piezoelectric oscillator, which is required for converging the ultrasound generated by the ultrasound probe in a beam form and determining transmission directivity. The pulse circuitry applies a drive signal (drive pulse) to the ultrasound transducers provided in the ultrasound probe 101 at a timing based on the rate pulse. By varying the delay time provided to each rate pulse through the delay circuitry, the transmission direction from surfaces of the piezoelectric oscillators can be freely adjusted.

The ultrasound transmission circuitry 110 is capable of freely varying an output intensity of the ultrasound wave based on the drive signal. In an ultrasound diagnostic apparatus, the effect of attenuation of the ultrasound wave in the living body P can be reduced by increasing the output intensity. By reducing the effect of attenuation of the ultrasound wave, the ultrasound diagnostic apparatus is capable of acquiring a reflected wave signal with a large S/N ratio at the time of reception.

In general, when an ultrasound wave is propagated through a living body P, the intensity of vibration of the ultrasound wave corresponding to the output intensity (which is also referred to as an "acoustic power") is attenuated. The attenuation of the acoustic power is caused by absorption, scattering, reflection, etc. The degree of reduction in acoustic power depends on the frequency of the ultrasound wave and the depth of the ultrasound wave in the radiation direction. For example, the degree of attenuation increases as the frequency of the ultrasound wave increases. Also, the degree of attenuation increases as the depth of the ultrasound wave in the radiation direction increases.

The ultrasound reception circuitry 120 is a processor that performs various processes on the reflected wave signal received by the ultrasound probe 101 and generates a receive signal. The ultrasound reception circuitry 120 generates a receive signal for the reflected wave signal of the ultrasound wave acquired by the ultrasound probe 101. Specifically, the ultrasound reception circuitry 120 is implemented by, for example, a preamplifier, an A/D converter, a demodulator, a beamformer, etc. The preamplifier performs a gain correction process by amplifying the reflected wave signal received by the ultrasound probe 101 for each channel. The A/D converter converts the gain-corrected reflected wave signal into a digital signal. The demodulator demodulates a digital signal. The beamformer provides, for example, the demodulated digital signal with a delay time required for determining reception directivity, and sums a plurality of digital signals provided with the delay time. Through the summation process by the beamformer, a receive signal is generated in which a component reflected from a direction corresponding to the reception directivity is enhanced.

The internal storage circuitry 130 includes, for example, a magnetic storage medium, an optical storage medium, a semiconductor memory, a processor-readable storage medium such as a semiconductor memory, etc. The internal storage circuitry 130 stores a program for realizing transmission and reception of the ultrasound, a program relating to a marker display process, various types of data, etc. Such programs and data may be stored in, for example, the internal storage circuitry 130 in advance. The programs and data may be, for example, stored in a non-volatile storage medium and distributed, and may be read from the non-volatile storage medium and installed into the internal storage circuitry 130. The internal storage circuitry 130 stores B-mode image data, contrast-enhanced image data, etc. generated by the processing circuitry 180 in accordance with an operation input via the input interface 150. The internal storage circuitry 130 can transfer the stored image data to the external device 104, etc. via the communication interface 170.

The internal storage circuitry 130 may be a drive, etc. which reads and writes various types of information from and to a portable storage medium such as a CD-ROM drive, a DVD drive, and a flash memory. The internal storage circuitry 130 may write the stored data into a portable storage medium, and store the data in the external device 104 via the portable storage medium.

The image memory 140 includes, for example, a magnetic storage medium, an optical storage medium, or a processor-readable storage medium such as a semiconductor memory. The image memory 140 stores image data corresponding to a plurality of frames taken immediately before a freeze operation and input through the input interface 150. The image data stored in the image memory 140 is, for example, continuously displayed (cine-displayed).

The internal storage circuitry 130 and the image memory 140 need not necessarily be implemented by separate storage devices. The internal storage circuitry 130 and the image memory 140 may be implemented by a single storage device. The internal storage circuitry 130 and the image memory 140 may be respectively implemented by a plurality of storage devices.

The input interface 150 receives various types of instructions from an operator through the input device 102. The input device 102 is, for example, a mouse, a keyboard, a panel switch, a slider switch, a trackball, a rotary encoder, an operation panel, or a touch command screen (TCS). The input interface 150 is connected to the processing circuitry 180 via, for example, a bus, converts an operation instruction that has been input by the operator into an electric signal, and outputs the electric signal to the processing circuitry 180. The input interface 150 is not limited to one that is connected to physical operation components such as a mouse, a keyboard, etc. Examples of the input interface include circuitry which receives an electric signal corresponding to an operation instruction that has been input from an external input device provided separately from the ultrasound diagnostic apparatus 1, and outputs the electric signal to the processing circuitry 180.

The output interface 160 is an interface that outputs an electric signal from the processing circuitry 180 to the display device 103. The display device 103 may be any display such as a liquid crystal display, an organic EL display, an LED display, a plasma display, a CRT display, etc. The display device 103 may be a touch-panel display which also functions as an input device 102. The output interface 160 is connected to the processing circuitry 180 via a bus, for example, and outputs an electric signal supplied from the processing circuitry 180 to the display device 103.

The communication interface 170 is, for example, connected to the external device 104 via the network NW, and performs data communications with the external device 104.

The processing circuitry 180 is, for example, a processor which functions as a nerve center of the ultrasound diagnostic apparatus 1. The processing circuitry 180 implements a function corresponding to a program stored in the internal storage circuitry 130 by executing the program. The processing circuitry 180 is equipped with, for example, a B-mode processing function 181, a Doppler processing function 182, an image generation function 183 (image generating unit), an acquisition function 184 (acquisition unit), a calculation function 185 (calculation unit), a display control function 186 (display control unit), and a system control function 187.

The B-mode processing function 181 is a function of generating B-mode data based on a receive signal received from the ultrasound reception circuitry 120. Through the B-mode processing function 181, the processing circuitry 180 performs an envelope detection process, a logarithmic compression process, etc. on the reception signal received from the ultrasound reception circuitry 120, and generates data (B-mode data) that expresses the signal intensity in terms of brightness. The generated B-mode data is stored in a raw data memory (not illustrated) as B-mode raw data on a two-dimensional ultrasound scan line (raster).

Through the B-mode processing function 181, the processing circuitry 180 is capable of performing contrast ultrasonography such as contrast harmonic imaging (CHI). That is, the processing circuitry 180 is capable of achieving separation between reflected wave data (a harmonic or subharmonic component) of the living body P into which a contrast agent has been administered and reflective wave data (a fundamental component) reflected from tissue in the living body P. This allows the processing circuitry 180 to extract the harmonic or subharmonic component from the reflected wave data of the living body P, and to generate B-mode data for generating contrast-enhanced image data.

The B-mode data for generating the contrast-enhanced image data is data that represents the signal intensity of a reflected wave reflected from a contrast agent in terms of brightness. The processing circuitry 180 is capable of generating B-mode data for generating tissue image data by extracting a fundamental component from the reflected wave data of the living body P.

At the time of performance of CHI, the processing circuitry 180 may extract a harmonic component based on a method different from the above-described method which uses a filtering process. In harmonic imaging, imaging techniques such as an amplitude modulation (AM) technique, a phase modulation (PM) technique, and a combination of the AM and PM techniques called an AMPM technique are employed.

In AM, PM, or AMPM techniques, ultrasound transmission to the same scan line is performed multiple times (at multiple rates) by varying the amplitude and the phase. This allows the ultrasound reception circuitry 120 to generate a plurality of items of reflected wave data and output the reflected wave data on each scan line. The processing circuitry 180 extracts a harmonic component by summing and/or subtracting the plurality of items of reflected wave data of the scanning lines in accordance with the modulation method. The processing circuitry 180 performs an envelope detection process, etc. on the reflected wave data of the harmonic component, thereby generating B-mode data.

When, for example, the PM technique is employed, the ultrasound transmission circuitry 110 transmits ultrasound waves of the same amplitude with an inverted phase and polarity, such as (−1, 1), two times over each scanning line in a scan sequence set by the processing circuitry 180. The ultrasound reception circuitry 120 generates reflected wave data corresponding to the transmission of "−1" and reflected wave data corresponding to the transmission of "1", and the processing circuitry 180 sums the two items of reflected wave data. Thereby, the fundamental component is eliminated, and a signal in which mainly a second harmonic component remains is generated. The processing circuitry 180 performs, for example, an envelope detection process on the generated signal, and generates B-mode data of CHI (B-mode data for generating a contrast-enhanced image).

The B-mode data of CHI is data that represents, in terms of brightness, the signal intensity of a reflected wave reflected from a contrast agent. When the PM technique is employed in CHI, the processing circuitry 180 is capable of generating B-mode data for generating tissue image data by, for example, filtering reflected wave data corresponding to the transmission of "1".

The Doppler processing function 182 is a function of performing frequency analysis of a receive signal received from the ultrasound reception circuitry 120 and thereby generating data (Doppler information) obtained by extracting motion information based on a Doppler effect of a moving object in a region of interest (ROI) set in the scan area. The generated Doppler information is stored in a raw data memory (not illustrated) as Doppler raw data on a two-dimensional ultrasound scan line.

The image generation function 183 is a function of generating B-mode image data based on data generated by the B-mode processing function 181. With the image generation function 183, the processing circuitry 180 converts (scan-converts) a scan line signal sequence for ultrasound scanning into, for example, a scan line signal sequence in a video format representatively used by television, etc. and generates image data (display image data) for display. Specifically, the processing circuitry 180 performs a raw-pixel conversion of the B-mode raw data stored in the raw data memory, such as a coordinate conversion corresponding to a mode of ultrasound scan by the ultrasound probe 101, thereby generating two-dimensional B-mode image data (also referred to as "ultrasound image data") consisting of pixels. In other words, the processing circuitry 180 generates, through the image generation function 183, a plurality of ultrasound images (medical images) respectively corresponding to a plurality of continuous frames, by transmission and reception of the ultrasound wave.

Also, the processing circuitry 180 converts image data into a video signal by performing various processes, such as dynamic range, brightness, contrast, γ-curve corrections, and an RGB conversion, on two-dimensional B-mode image data. The processing circuitry 180 causes the display device 103 to display the video signal. The processing circuitry 180 may generate a user interface (e.g., a graphical user interface, GUI) which allows an operator to input various instructions via an input apparatus, and causes the display device 103 to display the generated GUI.

The system control function 187 is a function of integrally controlling the entire operation of the ultrasound diagnostic apparatus 1. For example, the processing circuitry 180 controls, through the system control function 187, the ultrasound transmission circuitry 110 and the ultrasound reception circuitry 120 based on a parameter relating to transmission and reception of the ultrasound wave. The acquisition function 184, the calculation function 185, and the display control function 186 will be described later.

A basic configuration of the ultrasound diagnostic apparatus 1 according to the first embodiment has been described above. With such a configuration, the ultrasound diagnostic apparatus 1 according to the first embodiment is capable of reflecting, on an ultrasound image, the position of a lesion calculated from a mammographic image through the functions of processing circuitry to be described below.

In the processing circuitry 180, the acquisition function 184 is a function of acquiring a mammographic image. Specifically, the processing circuitry 180 acquires, for example, a mammographic image of a target patient stored in the PACS. At this time, the processing circuitry 180 acquires at least one of a mammographic image taken in a craniocaudal (CC) view (hereinafter referred to as a "CC view mammographic image") and a mammographic image taken in a mediolateral oblique (MLO) view (hereinafter referred to as an "MLO view mammographic image"), of the target patient. In the present embodiment, let us assume that CC view mammographic image is to be acquired.

Let us also assume that, in the mammographic image in the present embodiment, a region of interest is associated with, for example, a schematic diagram that schematically represents a breast (hereinafter referred to as a "body mark"). The body mark and the region of interest are displayed by being superimposed on a mammographic image. The "region of interest" being associated with the "mammographic image" may be rephrased as "the region of interest being set in the mammographic image".

Figure 13:
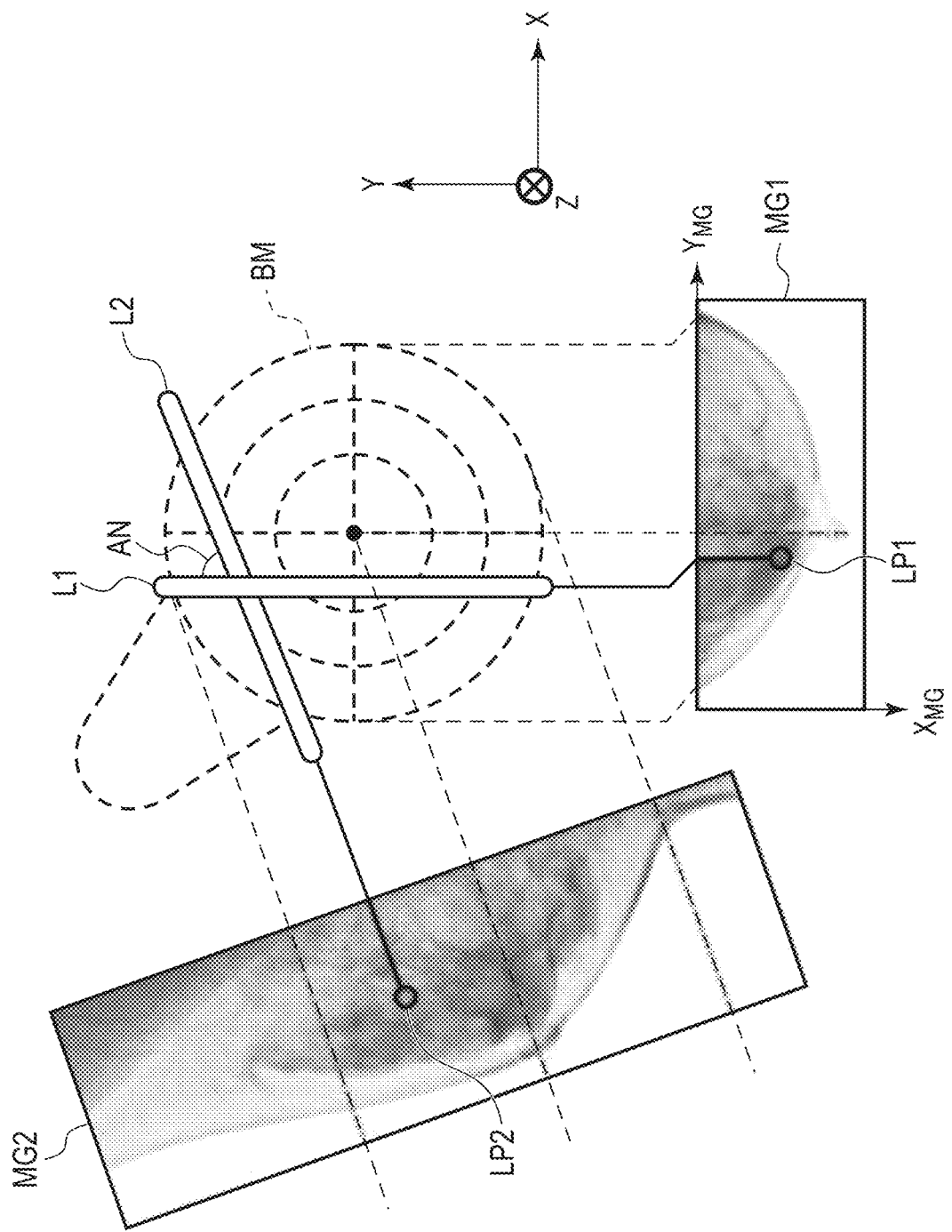
FIG. 13 is a diagram illustrating an example of a relationship between a body mark and a position of a region of interest on a mammographic image.

FIG. 13 is a diagram illustrating an example of a relationship between a body mark and a position of a region of interest on a mammographic image. A body mark BM in FIG. 13, which indicates a right breast, includes a circular region (hereinafter, a "breast region") representing the region of the breast and a substantially triangular region (hereinafter, an "axillary region") representing the region of the axillar. Hereinafter, in the body mark, a direction going from the left toward the right will be referred to as an "X direction", a direction going from the bottom toward the top will be referred to as a "Y direction", and a direction going from the front toward the back in a direction perpendicular to the X and Y directions will be referred to as a "Z direction".

Straight lines L1 and L2 are superimposed on the body mark BM by an ultrasound diagnosis support function. The straight line L1 represents an imaging direction with reference to a lesion position LP1 on a mammographic image MG1 taken in the CC view. The straight line L2 represents an imaging direction with reference to a lesion position LP2 on a mammographic image MG2 taken in the MLO view. An intersection between the straight line L1 and the straight line L2 corresponds to a lesion position on the body mark BM that is estimated based on the mammographic image MG1 and the mammographic image MG2.

The angle of an arm (arm angle) that supports an X-ray tube and an X-ray detector in a mammographic apparatus corresponds to an imaging direction, namely, the straight lines L1 and L2. Assuming that the arm angle in the CC view is 0 degrees, the arm angle in the MLO view is an angle AN at which the straight line L1 is tilted toward the straight line L2. The arm angle may be associated with a mammographic image.

In the processing circuitry 180, the calculation function 185 is a function of calculating a first distance from a region of interest to the body surface on a mammographic image, and calculating a second distance from a body surface to the region of interest on the ultrasound image. The processing circuitry 180 calculates a first distance from a region of interest to the body surface on a mammographic image, based on a region of interest set in the mammographic image. The first distance is, for example, calculated as an actual distance by using a scale of the mammographic image with respect to the straight line set on the image by a user or by image processing.

For example, the distance from the region of interest to the body surface in the CC view may be inconsistent with that in the MLO view. This is due to inconsistency in the direction of the straight line extending from the region of interest to the body surface. To resolve the inconsistency, the processing circuitry 180 may estimate a direction going from the region of interest to the body surface on the mammographic image by using the arm angle. The processing circuitry 180 may calculate the first distance based on the estimated direction.

Also, the processing circuitry 180 calculates the second distance from the body surface to the region of interest on the ultrasound image based on the calculated first distance. The second distance is calculated using, for example, an arithmetic expression by which a distance on a mammographic image and a distance on an ultrasound image can be mutually converted, taking into account the change in shape of a site to be examined during an examination based on a mammographic image and the change in shape of a site to be examined during an examination based on an ultrasound image. In other words, the processing circuitry 180 may calculate the second distance by employing deformation estimation of the breast based on a difference between a body position during an examination based on a mammographic image and that during an examination based on an ultrasound image.

In the processing circuitry 180, the display control function 186 is a function of displaying a marker indicating the depth of a lesion on an ultrasound image based on the calculated distance. The processing circuitry 180 displays a marker indicating the lesion depth in the ultrasound image, based on the calculated first distance. More specifically, the processing circuitry 180 displays a marker indicating the lesion depth by superimposing the marker on an ultrasound image, using the calculated second distance.

Examples of the method of displaying a marker on an ultrasound image include a method of displaying (overlaying) an overlay image including a marker on an ultrasound image. However, the configuration is not limited thereto, and a method of directly depicting a marker in the ultrasound image may be employed. The displaying of a marker on an ultrasound image may be rephrased as "displaying a marker in the ultrasound image", and the above-described two methods are encompassed by either of the expressions.

The processing circuitry 180 causes the display device 103 to display display image data generated by the image generation function 183. Specifically, the processing circuitry 180 may display the display image data alone on the display device 103, or display the display image data in the display device 103 in parallel with predetermined medical image data so as to be superimposed on medical image data. More specifically, the processing circuitry 180 may split the display region into two sections to allow the mammographic image and the ultrasound image to be displayed in parallel. Splitting the display region into two sections to allow two images to be displayed may be rephrased as "side-by-side display".

FIG. 2 is a flowchart illustrating an example of an operation of a marker display process according to the first embodiment. The marker display process is a process of displaying a lesion depth marker on an ultrasound image. The process shown in FIG. 2 is started, for example, upon receiving an instruction to perform a marker display process from the operator.

(Step ST110)

At the start of a marker display process, the processing circuitry 180 executes an acquisition function 184. Upon executing the acquisition function 184, the processing circuitry 180 acquires a mammographic image. Specifically, the processing circuitry 180 acquires a CC view mammographic image from the PACS.

(Step ST120)

After acquiring the mammographic image, the processing circuitry 180 executes a calculation function 185. Upon executing the calculation function 185, the processing circuitry 180 calculates a first distance from a region of interest to a body surface on the mammographic image based on a region of interest set in the acquired mammographic image.

Figure 3:
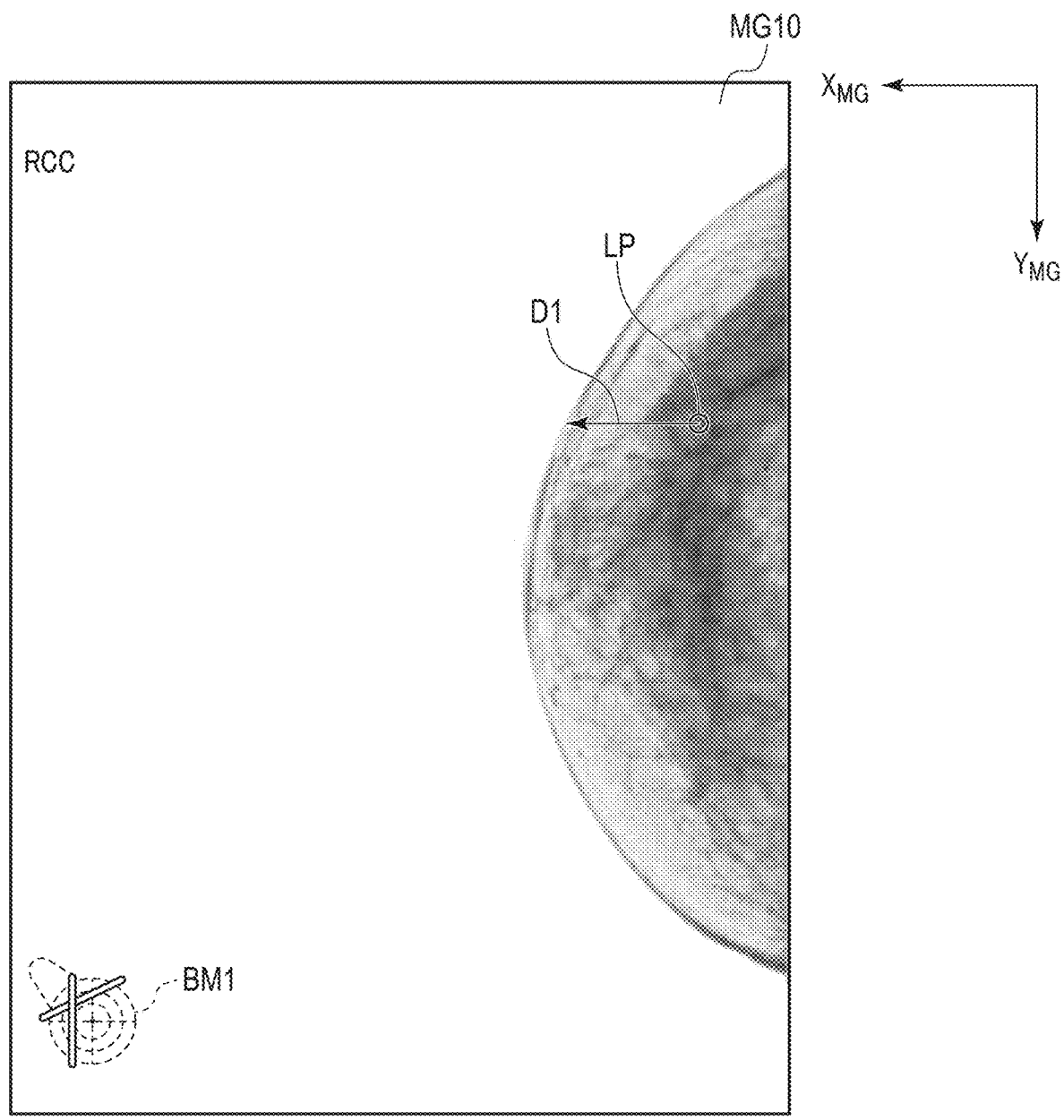
FIG. 3 is a diagram showing an example of a mammographic image according to the first embodiment.

FIG. 3 is a diagram showing an example of a mammographic image according to the first embodiment. In a mammographic image MG10 in FIG. 3, a right breast taken in the CC view is shown. In the mammographic image MG10, a body mark BM1 and a region of interest LP indicating the lesion position are superimposed. The intersection of the two straight lines shown in the body mark BM1 corresponds to the lesion position. In other words, the body mark BM1 indicates a position in a plane that is orthogonal to a depth direction of the region of interest LP on the mammographic image MG10. Hereinafter, in the mammographic image, a direction going from the right toward the left is defined as an $X_{MG}$ direction, and a direction going from the top toward the bottom is defined as a $Y_{MG}$ direction, with reference to the upper right in the mammographic image.

On the mammographic image MG10, the processing circuitry 180 extends a straight line from the region of interest LP in the $X_{MG}$ direction, and calculates a first distance D1 to the body surface. The position of the body surface on the mammographic image MG10 is determined by, for example, detecting a change in brightness value.

In this manner, the processing circuitry 180 calculates a first distance from the mammographic image. The processing by the calculation function 185 can be performed as an internal process of the processing circuitry 180, and need not be displayed on the display device 103.

(Step ST130)

After calculating the first distance, the processing circuitry 180 calculates a second distance from the body surface to the region of interest on the ultrasound image based on the calculated first distance. Specifically, the processing circuitry 180 calculates a second distance based on the first distance using an arithmetic expression by which a distance on the mammographic image and a distance on the ultrasound image can be mutually converted. This step is not essential and may be omitted.

(Step ST140)

After calculating the second distance, the processing circuitry 180 executes a display control function 186. Upon executing the display control function 186, the processing circuitry 180 displays a marker (lesion depth marker) indicating the lesion depth on the ultrasound image using the calculated second distance. After step ST140, the marker display process ends. The "lesion depth" may be rephrased as "depth of the region of interest".

When step ST130 is omitted, the processing circuitry 180 may display a marker indicating the lesion depth on the ultrasound image based on the first distance. That is, the processing circuitry 180 may display a marker indicating the lesion depth on the ultrasound image based on the first distance, regardless of whether or not step ST130 is omitted.

Figure 4:
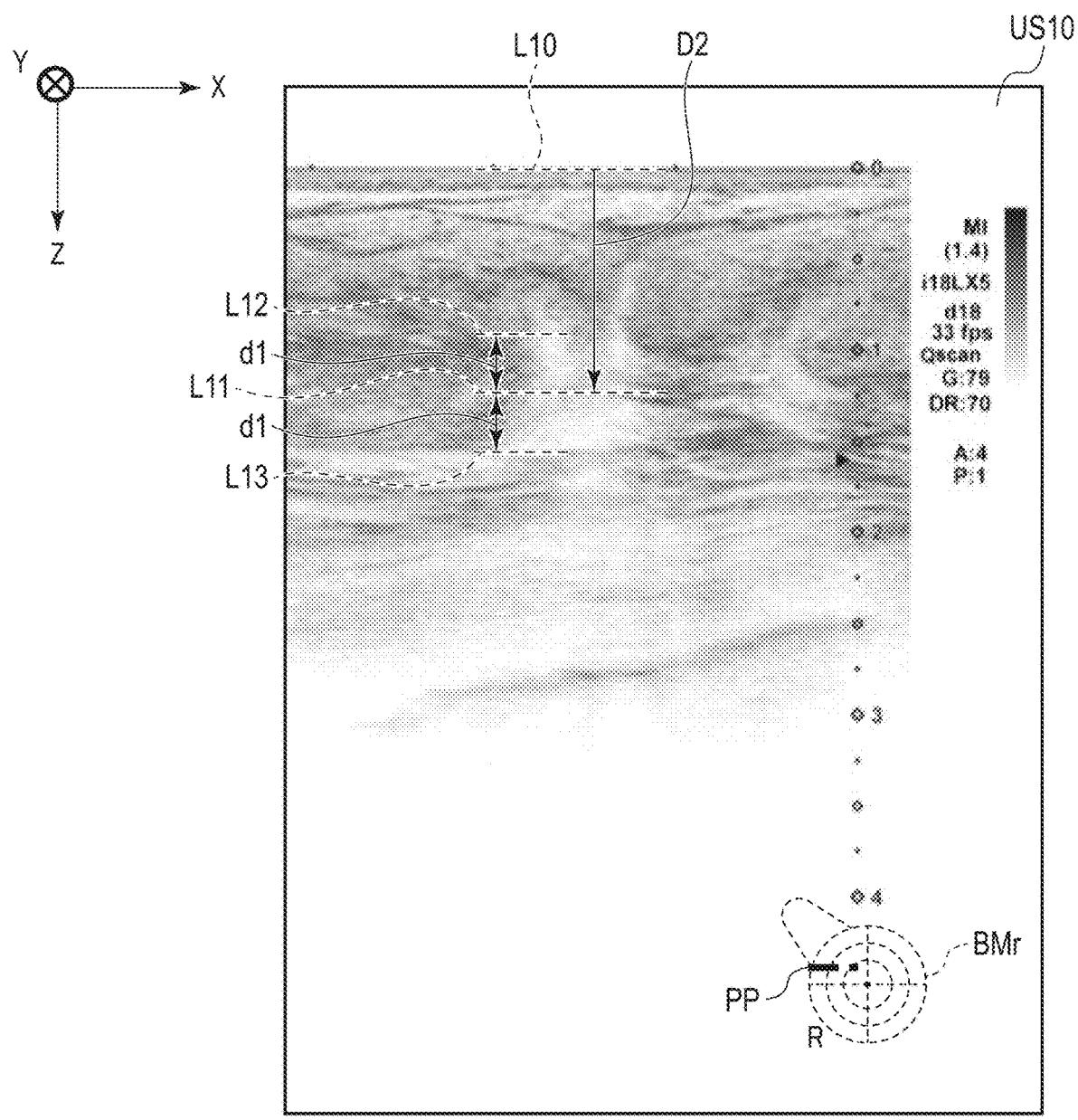
FIG. 4 is a diagram showing an example of an ultrasound image according to the first embodiment.

FIG. 4 is a diagram showing an example of an ultrasound image according to the first embodiment. In FIG. 4, a body mark BMr indicating a right breast is superimposed on the ultrasound image US10. On the body mark BMr, a probe position PP obtained by associating the position of the ultrasound probe on the body surface with the position on the body mark BMr is superimposed. Hereinafter, in an ultrasound image, a direction going from the left toward the right will be referred to as an "X direction", a direction going from the top toward the bottom will be referred to as a "Z direction", and a direction going from the front toward the back in a direction perpendicular to the X and Z directions will be referred to as a "Y direction".

The processing circuitry 180 sets, on the ultrasound image US10, a straight line L10 indicating the position of the body surface. After setting the straight line L10, the processing circuitry 180 sets a straight line L11 that is parallel to the straight line L10 at an interval of a second distance D2 in the +Z direction from the straight line L10. After setting the straight line L11, the processing circuitry 180 sets a straight line L12 that is parallel to the straight line L11 at an interval of a distance d1 in the −Z direction from the straight line L11. Similarly, the processing circuitry 180 sets a straight line L13 that is parallel to the straight line L11 at an interval of a distance d1 in the +Z direction from the straight line L11. The distance d1 may be, for example, a distance determined according to the size of the region of interest set in the mammographic image, or a discretionarily set distance.

FIG. 5 is a first display example in which a marker display process has been performed according to the first embodiment. A display region 10 in FIG. 5 includes an ultrasound image US10. On the ultrasound image US10, a straight-line marker M1 and a straight-line marker M2, respectively corresponding to the straight lines L12 and L13 in FIG. 4, are superimposed. The lesion depth marker corresponds to the straight-line markers M1 and M2. The region interposed between the straight-line markers M1 and M2 indicates a depth at which a lesion is positioned. This allows the user to easily identify the lesion position. In the display region 10, a body mark BM1 in FIG. 3 may be displayed in place of or in parallel with the body mark BMr.

Figure 6:
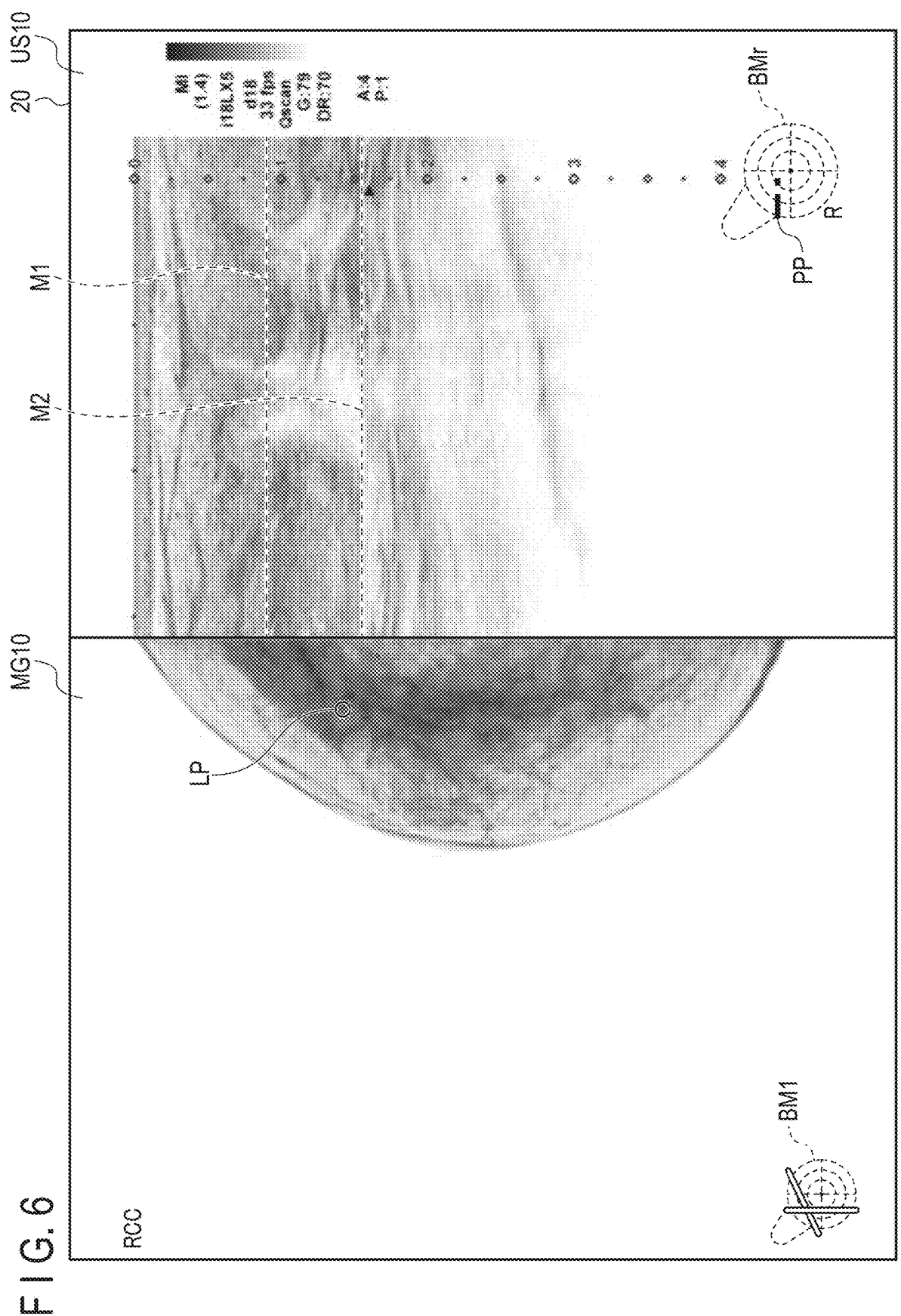
FIG. 6 is a second display example in which a marker display process has been performed according to the first embodiment.

FIG. 6 is a second display example in which a marker display process has been performed according to the first embodiment. A display region 20 in FIG. 6 includes a mammographic image MG10 and an ultrasound image US10. Specifically, in the display region 20, a mammographic image MG10 and an ultrasound image US10 are arranged at the left and the right, respectively, of the side-by-side display. This allows the user to identify the lesion position with reference to the body mark BM1 on the mammographic image MG10.

As described above, the ultrasound diagnostic apparatus according to the first embodiment calculates a first distance from a region of interest to the body surface on a mammographic image based on the region of interest set in the mammographic image, and displays, based on the first distance, a marker indicating the position of the region of interest in the ultrasound image as viewed in the depth direction. This eliminates the user having to read the depth position from the mammographic image, allowing the user to easily check the lesion in the ultrasound image.

In the first embodiment, an example of displaying a straight-line marker on an ultrasound image has been shown; however, the configuration is not limited thereto. For example, a graphic such as a rectangle or a circle may be used as the marker. A circular marker is, for example, a circle that has a radius of a distance d1 drawn from a given point on the straight line L11 in FIG. 4 as the center.

Second Embodiment

In the first embodiment, an explanation has been given of displaying a lesion depth marker on an ultrasound image through a marker display process. In the second embodiment, an explanation will be given of displaying a marker (lesion position marker) indicating a lesion position on an ultrasound image through a marker display process. The "lesion position" may be rephrased as a "position of the region of interest".

In the ultrasound diagnostic apparatus according to the second embodiment, let us assume that a mammographic image and an ultrasound image are aligned. A mammographic image and an ultrasound image being aligned refers to a state in which coordinates of a region of interest on the mammographic image and spatial coordinates of the ultrasound probe are associated.

Specifically, let us assume that the ultrasound diagnostic apparatus according to the second embodiment includes a magnetic transmitter in the apparatus main body, and that the ultrasound probe includes a magnetic sensor. The magnetic transmitter generates a pulsed magnetic field. The magnetic sensor detects the position and angle of the ultrasound probe with reference to predetermined spatial coordinates of a space in which the pulsed magnetic field occurs. Thereby, in the ultrasound diagnostic apparatus according to the second embodiment, the mammographic image and the ultrasound image are aligned.

FIG. 7 is a flowchart illustrating an example of an operation of a marker display process according to the second embodiment. The marker display process is a process of displaying a lesion position marker on an ultrasound image. The process shown in FIG. 7 is started, for example, upon receiving an instruction to perform a marker display process from the operator.

(Step ST210)

At the start of a marker display process, the processing circuitry 180 executes an acquisition function 184. Upon executing the acquisition function 184, the processing circuitry 180 acquires a CC view mammographic image.

(Step ST220)

After acquiring the CC view mammographic image, the processing circuitry 180 acquires an MLO view mammographic image. Step ST210 and step ST220 may be performed simultaneously, and two mammographic images taken from two different directions may be acquired.

(Step ST230)

After acquiring the MLO view mammographic image, the processing circuitry 180 executes a calculation function 185. Upon executing the calculation function 185, the processing circuitry 180 calculates, based on a region of interest set in the acquired mammographic image, a first distance from a region of interest to a body surface on the mammographic image. The processing circuitry 180 calculates the first distance using at least one of the CC view mammographic image and the MLO view mammographic image. Since the processing at step ST230 is similar to the above-described processing at ST120, a detailed description thereof will be omitted.

(Step ST240)

After calculating the first distance, the processing circuitry 180 calculates a second distance from the body surface to the region of interest on the ultrasound image based on the calculated first distance. Specifically, the processing circuitry 180 calculates a second distance based on the first distance using an arithmetic expression by which a distance on a mammographic image and a distance on an ultrasound image can be mutually converted.

(Step ST250)

After calculating the second distance, the processing circuitry 180 calculates three-dimensional position information on the ultrasound image based on the calculated second distance, position information on the region of interest set in the CC view mammographic image, and position information on the region of interest set in the MLO view mammographic image.

Specifically, the processing circuitry 180 calculates a position on a two-dimensional plane corresponding to a region of interest on a body mark BM1 based on position information on a region of interest set in the CC view mammographic image, and the position information of the region of interest set in the MLO view mammographic image. After calculating the position on the two-dimensional plane, the processing circuitry 180 calculates a position on a three-dimensional space based on the position on the two-dimensional plane and the calculated second distance.

Figure 8:
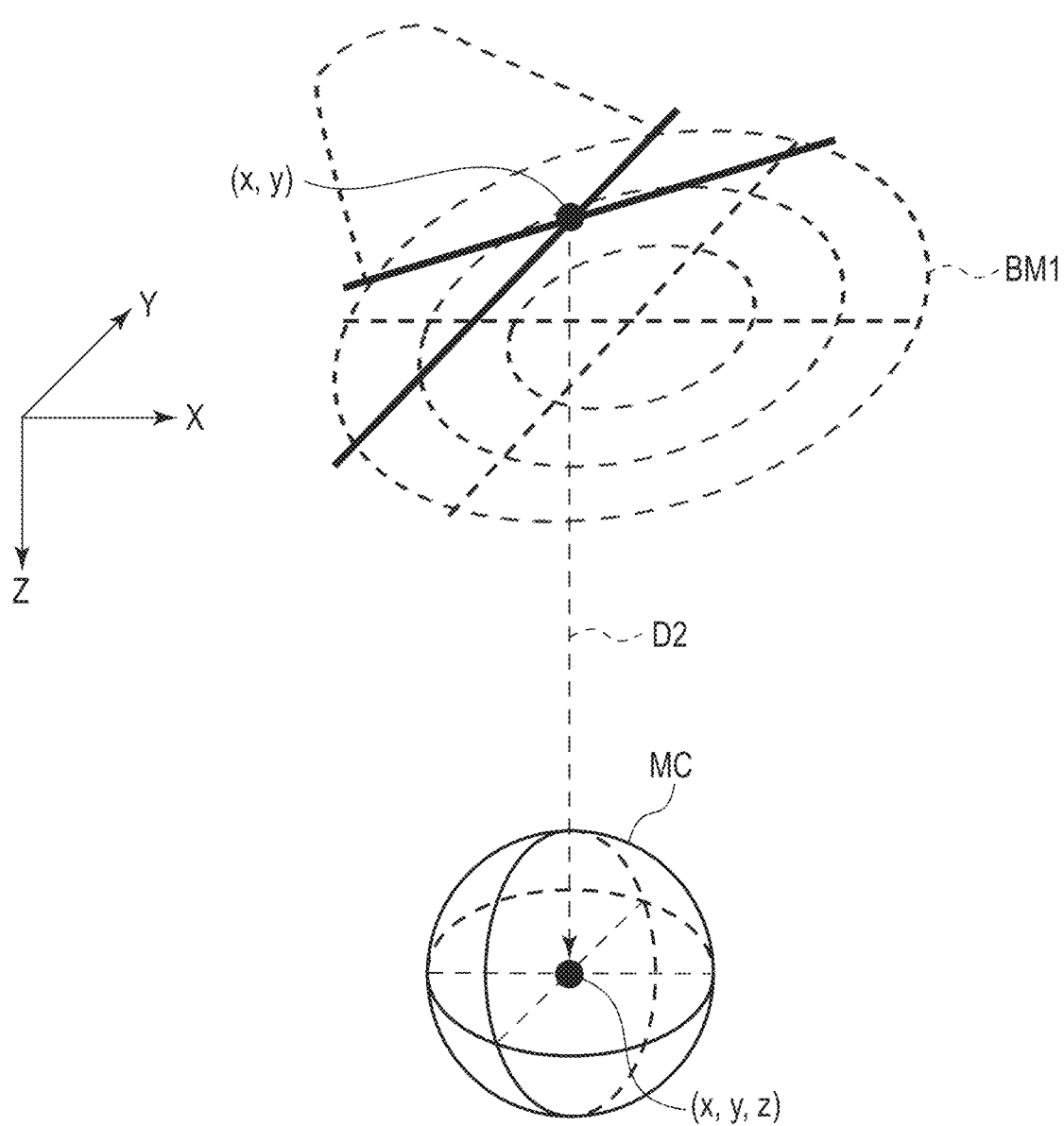
FIG. 8 is a diagram illustrating an example of a relationship between a position of a region of interest on a body mark and a three-dimensional marker according to the second embodiment.

FIG. 8 is a diagram illustrating an example of a relationship between a position of a region of interest on a body mark and a three-dimensional marker according to the second embodiment. Assuming that the body mark BM1 in FIG. 8 is the body surface, a +Z direction corresponds to the depth direction in the body. The position on the two-dimensional plane is, for example, a position (x, y) of the region of interest on the body mark BM1. The position in the three-dimensional space is, for example, a central position (x, y, z) of a three-dimensional marker MC.

(Step ST260)

After calculating three-dimensional position information, the processing circuitry 180 executes a display control function 186. Upon executing the display control function 186, the processing circuitry 180 displays a lesion position marker corresponding to the position information of the probe on the ultrasound image, based on the calculated three-dimensional position information. After step S260, the marker display process ends.

Figure 9:
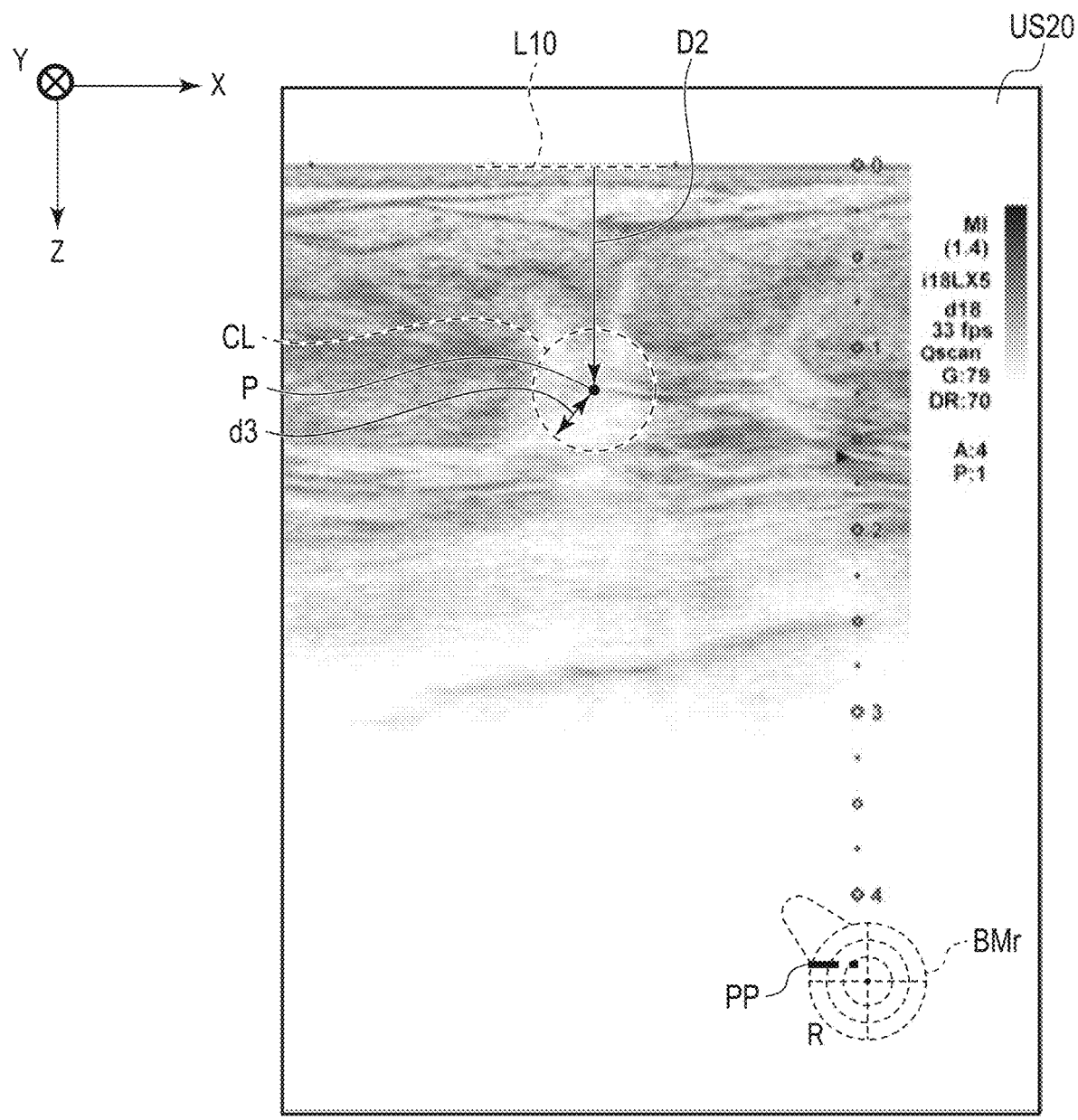
FIG. 9 is a diagram showing an example of an ultrasound image according to the second embodiment.

FIG. 9 is a diagram showing an example of an ultrasound image according to the second embodiment. In FIG. 9, a body mark BMr is superimposed on an ultrasound image US20. A probe position PP is superimposed on the body mark BMr.

The processing circuitry 180 sets, on the ultrasound image US20, a straight line L10 representing the position of the body surface. After setting the straight line L10, the processing circuitry 180 sets a depth position P at an interval of a second distance D2 in the +Z direction from the straight line L10. The depth position P corresponds to a position z of a three-dimensional marker MC. After setting the depth position P, the processing circuitry 180 sets a circumference CL of a circle that has a radius d3 drawn from the depth position P as the center. The circumference CL corresponds to a circumference of a given cross section of the three-dimensional marker MC.

Figure 10:
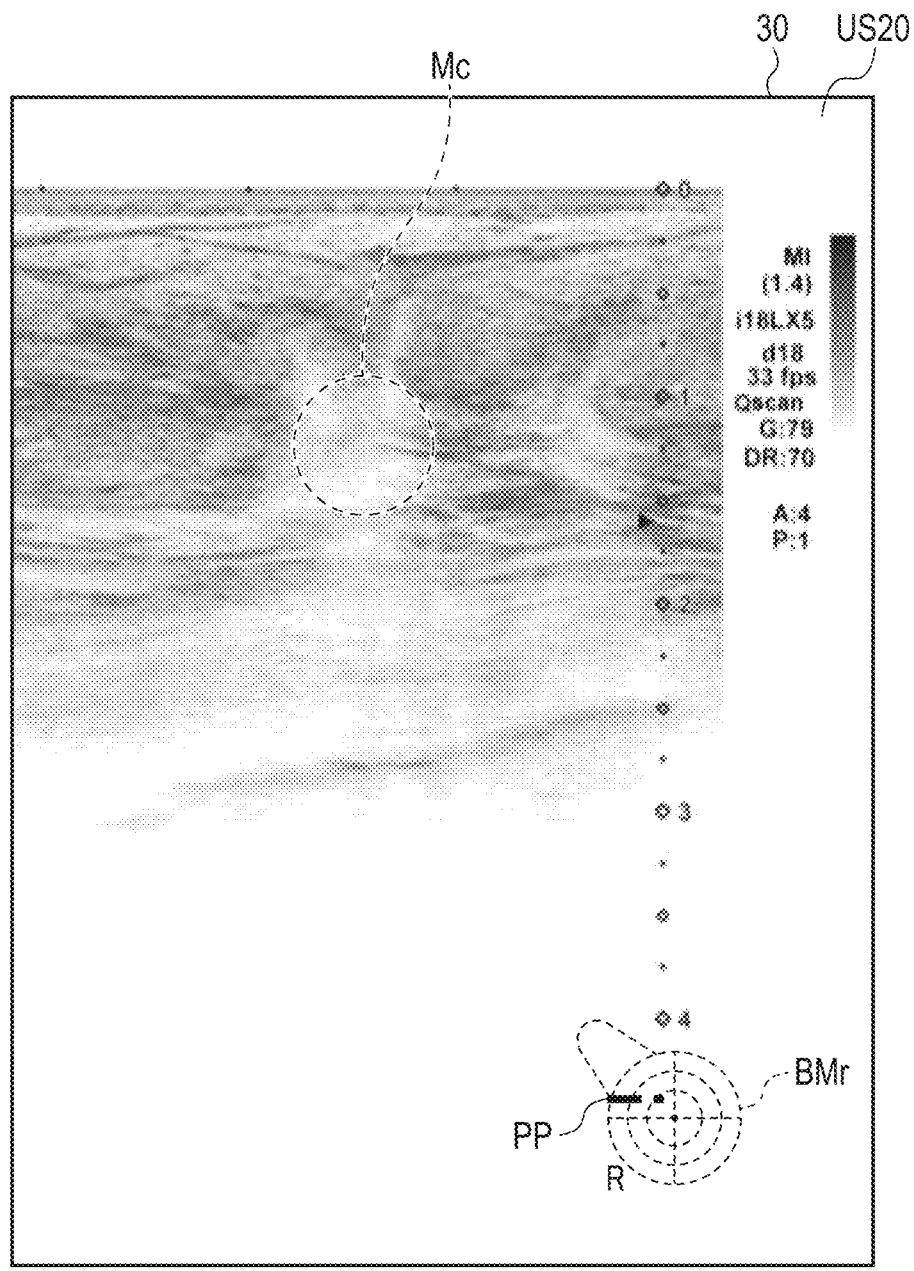
FIG. 10 is a first display example in which a marker display process has been performed according to the second embodiment.

FIG. 10 is a first display example in which a marker display process has been performed according to the second embodiment. A display region 30 in FIG. 10 includes an ultrasound image US20. On the ultrasound image US20, a circular marker Mc corresponding to a circumference CL in FIG. 9 is superimposed. The lesion position marker corresponds to the circular marker Mc. The region surrounded by the circular marker Mc indicates a lesion position. In the display region 30, a body mark BM1 in FIG. 3 may be displayed in place of or in parallel with the body mark BMr.

The size of the circular marker Mc may be varied according to, for example, the position of the ultrasound probe. Specifically, the size of the circular marker Mc is maximized when the probe position PP overlaps the lesion position on the body mark BMr (i.e., the position of the intersection of the two straight lines shown in the body mark BM1 in FIG. 3), and decreases as the overlapping lesion position and probe position PP are further distanced from each other. The maximum-size circular marker may be constantly displayed as a guide.

Also, the color of the circular marker Mc may be varied according to, for example, the position of the ultrasound probe. Specifically, the circular marker Mc turns green when the probe position PP overlaps the lesion position, and changes from green to yellow to red as the overlapping lesion position and probe position PP are further distanced from each other.

In other words, the circular marker Mc varies at least one of the size and the color according to the position of the ultrasound probe. This allows the user to identify the lesion position easily, compared to when only the depth position of the lesion position is indicated.

Figure 11:
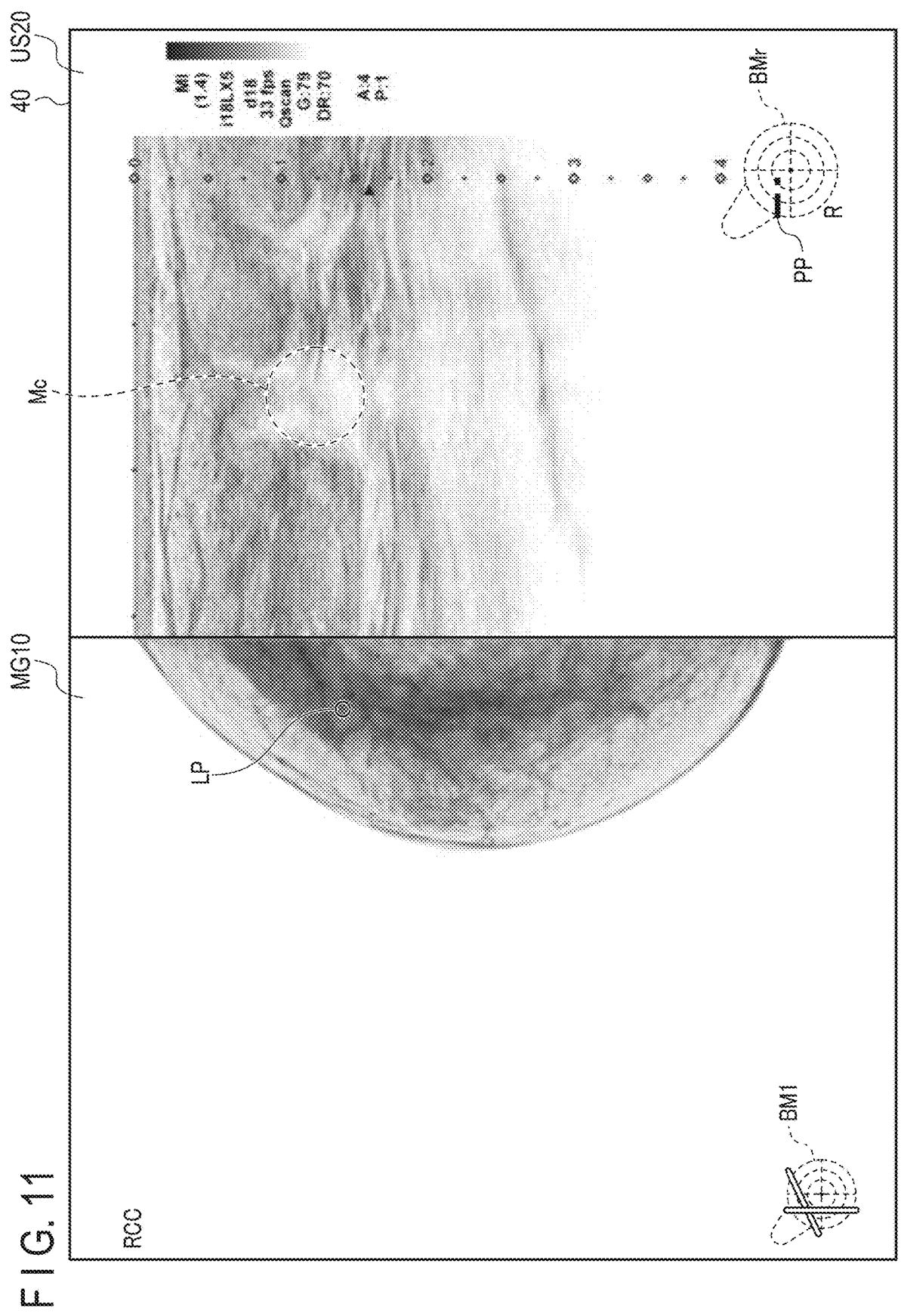
FIG. 11 is a second display example in which a marker display process has been performed according to the second embodiment.

FIG. 11 is a second display example in which a marker display process has been performed according to the second embodiment. A display region 40 in FIG. 11 includes a mammographic image MG10 and an ultrasound image US20. Specifically, in the display region 40, a mammographic image MG10 and an ultrasound image US20 are arranged at the left and the right, respectively, of the side-by-side display. This allows the user to identify the lesion position with reference to the body mark BM1 on the mammographic image MG10.

As described above, the ultrasound diagnostic apparatus according to the second embodiment acquires two mammographic images taken from two different directions, calculates a first distance from a region of interest to the body surface on one of the mammographic images based on the region of interest set in the one of the mammographic images, calculates a second distance from the body surface to the region of interest on an ultrasound image based on the first distance, calculates three-dimensional position information on the ultrasound image based on the second distance and position information of the region of interest set in each of the two mammographic images, and displays a marker on the ultrasound image based on the calculated three-dimensional position information. This eliminates the user having to read the depth position from the mammographic image, allowing the user to easily check the lesion in the ultrasound image.

In the second embodiment, an example in which a circular marker is displayed on an ultrasound image has been shown; however, the configuration is not limited thereto. For example, the marker may be a rectangle or in a shape corresponding to a region depicted by the color Doppler technique.

Application Example

In the first and second embodiments, a marker display process on an ultrasound image has been described. In an application example, a case will be described where transmission and reception of the ultrasound are controlled according to the display position of a marker.

Through the system control function 187, the processing circuitry 180 controls transmission and reception of the ultrasound using parameters relating to transmission and reception of the ultrasound according to the display position of the marker. The control of the transmission and reception of the ultrasound refers to, for example, control of the ultrasound transmission circuitry 110 and the ultrasound reception circuitry 120. Specifically, the processing circuitry 180 controls transmission and reception of the ultrasound using a focus position corresponding to the display position of the marker.

In this application example, since the transmission and reception of the ultrasound are controlled according to the display position of the marker, the user can perform an examination using optimum parameters, without setting parameters relating to the transmission and reception of the ultrasound.

Third Embodiment

In the first and second embodiments, a marker display process performed in processing circuitry included in an ultrasound diagnostic apparatus has been described. In the third embodiment, a marker display process performed in processing circuitry included in an image processing apparatus will be described.

Figure 12:
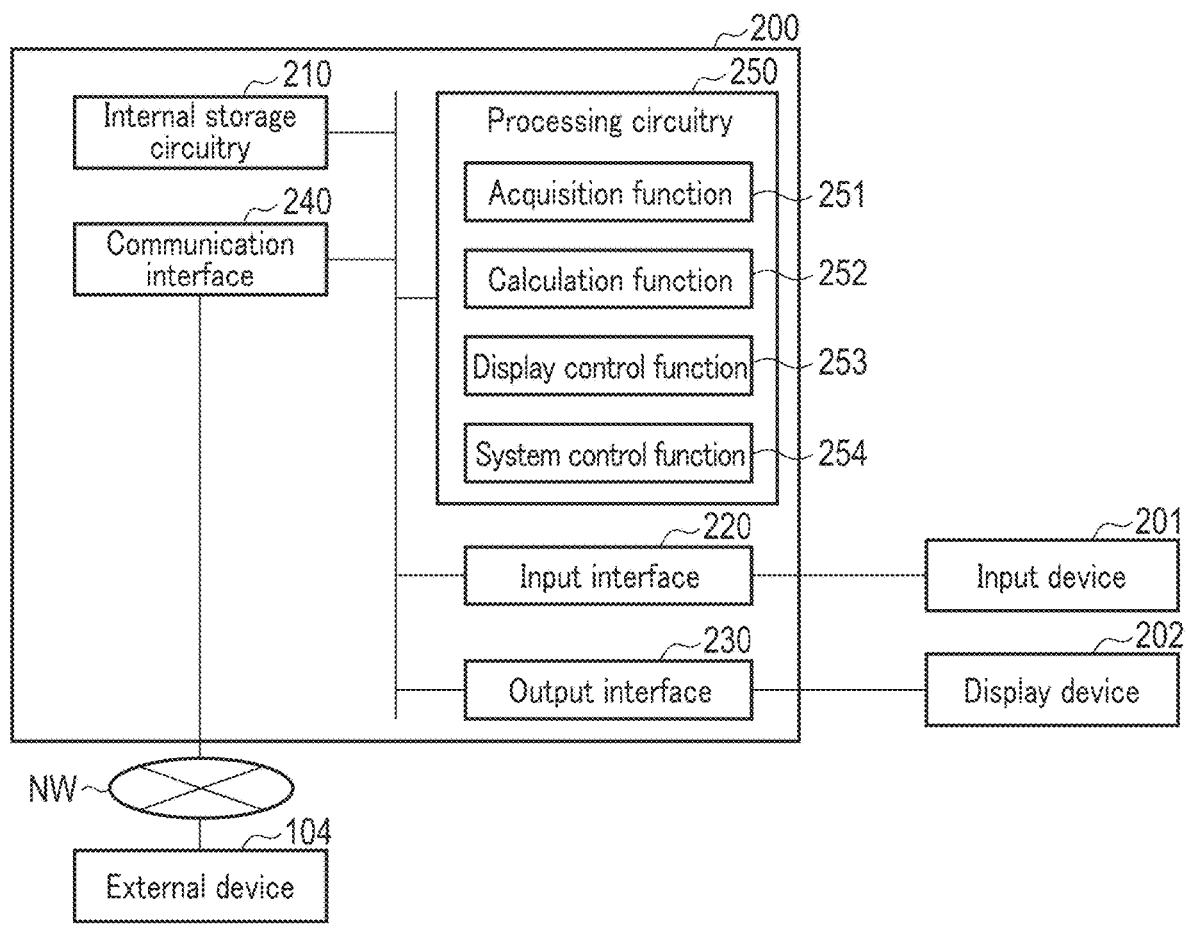
FIG. 12 is a block diagram showing a configuration example of an image processing apparatus according to a third embodiment.

FIG. 12 is a diagram showing a configuration example of an image processing apparatus according to a third embodiment. The image processing device 200 of FIG. 13 is connected to an input device 201 and a display device 202. The image processing device 200 is connected to an external device 104 via a network NW. The input device 201 and the display device 202 are substantially the same as those of the input device 102 and the display device 103 of FIG. 1, and the description thereof will be omitted.

The image processing device 200 includes internal storage circuitry 210, an input interface 220, an output interface 230, a communication interface 240, and processing circuitry 250.

The internal storage circuitry 210 includes, for example, a magnetic storage medium, an optical storage medium, a semiconductor memory, a processor-readable storage medium such as a semiconductor memory, etc. The internal storage circuitry 210 stores, for example, a program relating to a marker display process.

The input interface 220 receives various types of instructions from an operator through the input device 201. The input interface 220 is connected to the processing circuitry 250 via, for example, a bus, converts an operation instruction that has been input by the operator into an electric signal, and outputs the electric signal to the processing circuitry 250.

The output interface 230 is, for example, an interface that outputs an electric signal from the processing circuitry 250 to the display device 202. The output interface 230 is connected to the processing circuitry 250 via a bus, for example, and outputs an electric signal supplied from the processing circuitry 250 to the display device 202.

The communication interface 240 is connected to the external device 104 via the network NW, for example, and performs data communication with the external device 104.

The processing circuitry 250 is, for example, a processor that acts as a nerve center of the image processing device 200. The processing circuitry 250 executes a program of a marker display process stored in the internal storage circuitry 210 to realize a function corresponding to the program. The processing circuitry 250 is equipped with, for example, an acquisition function 251, a calculation function 252, a display control function 253, and a system control function 254.

The system control function 254 is a function of integrally controlling the entire operation of the image processing device 200. Since the acquisition function 251, the calculation function 252, and the display control function 253 are substantially the same as those of the acquisition function 184, the calculation function 185, and the display control function 186 described in the first and second embodiments, the descriptions thereof will be omitted.

As described above, the image processing apparatus according to the third embodiment is expected to offer an advantageous effect similar to those of the first and second embodiments.

The image processing apparatus according to the present embodiment corresponds to some of the configurations extracted from the ultrasound diagnostic apparatus according to the first and second embodiments.

In other words, the ultrasound diagnostic apparatus corresponds to the configuration of the image processing apparatus to which the configuration of ultrasound diagnosis is added.

According to at least one of the above-described embodiments, it is possible to improve convenience in mammographic image diagnosis using an ultrasound image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions.

The accompanying claims and their equivalents are intended to cover such forms or modifications as would fall within the scope and spirit of the inventions.

The invention claimed is:

1. An image processing apparatus, comprising:
processing circuitry configured to:
calculate, based on a region of interest set in a mammographic image, a first distance from the region of interest to a body surface on the mammographic image; and
display, in an ultrasound image, a marker indicating a position of the region of interest as viewed in a depth direction based on the first distance,
wherein the marker includes a first straight-line marker and a second straight-line marker indicating a depth or a position of the region of interest on the ultrasound image, a region interposed between the first straight-line marker and the second straight-line marker indicates a depth at which a lesion corresponding to the region of interest is positioned, and the processing circuitry is further configured to display the first straight-line marker and the second straight-line marker on the ultrasound image so as to indicate the depth at which the lesion is positioned.

2. The image processing apparatus according to claim 1, wherein the processing circuitry is further configured to display a body mark indicating a position in a plane that is orthogonal to the depth direction of the region of interest on the mammographic image, together with the ultrasound image.

3. The image processing apparatus according to claim 1, wherein the processing circuitry is further configured to:
calculate a second distance from the body surface to the region of interest on the ultrasound image based on the first distance; and
display the marker in the ultrasound image using the second distance.

4. The image processing apparatus according to claim 3, wherein the processing circuitry is further configured to calculate the second distance by employing deformation estimation of a breast based on a difference between a body position during an examination based on the mammographic image and a body position during an examination based on the ultrasound image.

5. The image processing apparatus according to claim 3, wherein the processing circuitry is further configured to:
calculate three-dimensional position information on the ultrasound image based on the second distance and position information of a region of interest set in each of two mammographic images taken from two different directions; and
display the marker on the ultrasound image based on the three-dimensional position information.

6. The image processing apparatus according to claim 1, wherein the processing circuitry is further configured to display the mammographic image and the ultrasound image on which the marker is superimposed in parallel.

7. The image processing apparatus according to claim 1, wherein the processing circuitry is further configured to display the marker according to a size of the region of interest.

8. The image processing apparatus according to claim 1, wherein the marker indicates a depth or a position of the region of interest on the ultrasound image.

9. The image processing apparatus according to claim 1, wherein the marker is a straight line or a circle.

10. The image processing apparatus according to claim 1, wherein the processing circuitry is further configured to:
- estimate, using an arm angle associated with the mammographic image, a direction from the region of interest to the body surface on the mammographic image; and
- calculate the first distance based on the estimated direction.

11. An ultrasound diagnostic apparatus, comprising:
- the image processing apparatus according to claim 1; and
- an ultrasound probe used for acquisition of the ultrasound image.

12. The ultrasound diagnostic apparatus according to claim 11, further comprising control circuitry configured to control ultrasound transmission and reception using a parameter relating to the ultrasound transmission and reception corresponding to a display position of the marker.

13. The ultrasound diagnostic apparatus according to claim 12, wherein the parameter is a focus position, and the control circuitry is further configured to control the ultrasound transmission and reception using the focus position corresponding to the display position of the marker.

14. The ultrasound diagnostic apparatus according to claim 11, wherein the processing circuitry is further configured to vary at least one of a size and a color of the marker according to a position of the ultrasound probe.

15. An image processing method, comprising:
- calculating, based on a region of interest set in a mammographic image, a first distance from the region of interest to a body surface on the mammographic image; and
- displaying, in an ultrasound image, a marker indicating to a position of the region of interest in an ultrasound image as viewed in a depth direction based on the first distance,
- wherein the marker includes a first straight-line marker and a second straight-line marker indicating a depth or a position of the region of interest on the ultrasound image, a region interposed between the first straight-line marker and the second straight-line marker indicates a depth at which a lesion corresponding to the region of interest is positioned, and the processing circuitry is further configured to display the first straight-line marker and the second straight-line marker on the ultrasound image so as to indicate the depth at which the lesion is positioned.

16. The image processing apparatus according to claim 2, wherein the processing circuitry is further configured to split a display region into two sections to allow the mammographic image and the ultrasound image to be displayed in parallel.

* * * * *